United States Patent [19]

Clumpner et al.

[11] Patent Number: 5,080,834

[45] Date of Patent: Jan. 14, 1992

[54] BRANCHED ETHER ESTERS AS VISCOSITY INDEX MODIFIERS

[75] Inventors: J. Michael Clumpner, Delavan, Wis.; Anthony J. O'Lenick, Jr., Lilburn, Ga.

[73] Assignee: Lee Partnership, Lake Geneva, Wis.

[21] Appl. No.: 599,418

[22] Filed: Oct. 18, 1990

[51] Int. Cl.$^5$ .............................................. C09F 5/08
[52] U.S. Cl. ................... 260/410.6; 560/198; 560/199; 568/413; 568/593; 568/613; 524/317; 524/357
[58] Field of Search ............... 260/410.6; 560/198, 560/199; 568/413, 593, 613; 524/317, 357

[56] References Cited

U.S. PATENT DOCUMENTS

| | | | |
|---|---|---|---|
| 4,181,618 | 1/1980 | Durand | 524/317 |
| 4,207,196 | 6/1980 | Sudekum | 260/410.6 |
| 4,212,816 | 7/1980 | Hentschel | 260/410.6 |
| 4,631,159 | 4/1991 | Berens et al. | 568/593 |

Primary Examiner—Jose G. Dees
Assistant Examiner—Debroah D. Carr

[57] ABSTRACT

The present invention deals with novel internal branched ether esters based upon novel ether alcohols. These materials are useful as viscosity index modifiers where outstanding liquidity, resistance to oxidation, and minimal variation in viscosity as a function of temperature is required.

15 Claims, No Drawings

BRANCHED ETHER ESTERS AS VISCOSITY INDEX MODIFIERS

BACKGROUND OF THE INVENTION

1. Field of the Invention

The present invention deals with novel branched ether ester compounds useful as viscosity index modifiers. These esters are derived from novel branched ether alcohols. It is because of the internal location of the branched ether group in these ether esters that these materials are very efficient viscosity index modifying materials. They have low viscosity, are stable to oxidation and exhibit minimal variation in viscosity as a function of temperature. All of these properties are required for a viscosity index modifier.

2. Description of the Art and Practices

Viscosity index modifiers are known in the art. Typical teachings are as follows:

U.S. Pat. No. 4,207,196, to Sudekum issued June 10, 1980 teaches that ethylene/alpha olefin polymers are useful in viscosity index modification.

U.S. Pat. No. 4,212,816 to Hentschel issued July 15, 1980, teaches that pentaerythritol esters of carboxylic acids are useful as viscosity index modifiers.

U.S. Pat. No. 4,181,618 to Durand issued Jan. 1, 1980, teaches that graft copolymers of vinyl compounds are useful as viscosity index modifiers.

U.S. Pat. No. 4,63,159 issued April 1981 to Berens et al teaches that certain aliphatic polyol compounds reacted with branched monocarboxylic acid form esters useful in automatic transmission fluids.

None of these materials shown to be useful as viscosity index modifiers are as effective as the highly branched ether esters taught by the current invention.

There are several factors known about liquidity in esters. When made to a given molecular weight, the highest viscosity esters are those derived from saturated linear alcohols. This class of compounds also exhibit a wide change in viscosity as a function of temperature. It is for these reasons that esters derived from saturated linear alcohols are least desirable as viscosity index modifiers.

Pentaerythritol, a highly branched four hydroxyl group containing alcohol is sometimes used to obtain an improvement in viscosity over saturated alcohols. The improvement is only partial and there are difficulties in controlling the reaction if less than four equivalents of acid is added.

The next improvement is to base the ester upon oxo alcohols. Oxo alcohols are well known to those skilled in the art. They contain about 20-30% branching at the alpha position. The branching is methyl. Esters derived from this type of raw material are the more liquid than esters derived from saturated linear alcohols if the esters have the same molecular weight.

Finally, esters based upon guerbet alcohols are the most liquid of the groups discussed. There are many references to the use of gurebet alcohols to make esters for use in a variety of lubricating applications. The useful property of guerbet alcohols in lubricating applications is the beta branch and the liquidity it renders.

Guerbet Alcohols are known materials which have a high degree of regiospecific beta branching. They have been known since the 1890's when Marcel Guerbet first synthesized them. (M. Guerbet, C. R. Acad. Sci. Paris, 128, 511; 1002 (1899)). These materials are high in molecular weight and are liquid to very low temperatures.

The guerbet reaction gives very specific branching in the alcohol as shown;

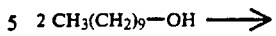

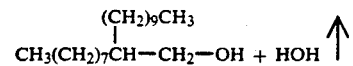

As can be seen by the above reaction the molecules have substitution on the second carbon from the hydroxyl group. This branching has been found to be critical to the preparation of a product having the desired lubrication and oxidative stability properties. If the branching were on the same carbon as the hydroxyl group, the hydroxyl group would be a secondary one and would be very hindered and has low reactivity. As one moves the branch position away from the beta carbon, the liquidity, lubricity and metal substantivity decreases. If the branch is lower alkyl like methyl in some oxo alcohols, there is little increase in the liquidity, lubricity and metal substantivity over normal alcohols having the same number of carbons. Additionally, the oxo process gives only some beta branching (between 1 and 28%) the guerbet process gives essentially 100% product.

U.S. Pat. No. 4,425,458 issued January 1984 to Lindner et al teaches that certain diesters of guerbet alcohols are useful as lubricants in polycarbonate applications. Additionally, U.S. Pat. No. 4,767,815 issued August 1988, to O'Lenick teaches that certain guerbet ether esters are likewise useful as polycarbonate lubricants.

U.S. Pat. No. 4,800,077 issued January 1989, to O'Lenick et al teaches that guerbet alcohols can be used to prepare certain conditioning quaternary compounds.

U.S. Pat. No. 4,868,236 issued September 1989, to O'Lenick teaches that certain guerbet alcohol citrate esters are useful in plastic lubrication.

U.S. Pat. Nos. 4,731,190 and 4,830,769 both to O'Lenick teaches that certain alkoxylate esters are useful as lubricants useful in facilitating the working of metal. Guerbet alcohol derived esters have not enjoyed widespread acceptance in viscosity index modification applications.

Surprisingly, the compounds of the present invention are superior to esters of guerbet alcohols of the same molecular weight. Hence they are very useful as viscosity index modifiers.

OBJECT OF THE INVENTION

It is the object of the present invention to provide a series of novel branched ether esters, which have very low viscosities over a range of temperatures. These materials are very effective viscosity index modifiers.

THE INVENTION

The present invention relates to a particular group of high molecular weight beta branched internal ether esters which are derived from high molecular weight internal branched ether alcohols. These compounds have one alkyl group and one ether alkyl group branch which differentiates our esters from esters derived from guerbet alcohols. Guerbet alcohols have two alkyl branches derivatives in the beta position. The presence of the ether function has a profound effect upon viscosity of the ester and consistency of viscosity as a function of temperature. The unique ether beta branch also differentiates our esters from esters derived from oxo alcohols. Oxo alcohols have no ether group. The position of the branched ether group also distinguishes these materials from alkoxylated fatty alcohol esters. The latter has the ether linkage on the terminal portion of the molecule and has a lower alkyl group between the oxygen groups.

$$R-(-O-CH_2-CH(CH_3))_x-OH$$

$$R-(-O-CH_2-CH_2-)_x-OH$$

An additional aspect of the invention is the surprising efficiency of these branched ether esters as viscosity index modifiers.

$$\underset{CH_3(CH_2)_7CH-CH_2OH}{\overset{(CH_2)_9CH_3}{|}} \quad \begin{array}{l}\text{A Guerbet Alcohol}\\\text{(Dialkyl beta branched)}\end{array}$$

Aldol Alcohol (Alkyl ether alkyl beta branched)

$$\underset{R'-CH-CH_2-O-H}{\overset{R''}{|}}$$

R' is $H-[-CH_2-\underset{CH_3}{\overset{|}{CH}}-]_n-CH_2(\underset{CH_3}{\overset{|}{CH}})-(CH_2)_2-$ R'' is $-O-(CH_2)_4-\underset{CH_3}{\overset{|}{CH}}-CH_2-[-\underset{CH_3}{\overset{|}{CH}}-CH_2]_m-H$ It will be understood by those skilled in the art that the above definition or R' and R'' will also include several other positional isomers.

The compounds of the current invention are the esterification product of a new series of branched ether alcohols and their alkoxylates recently developed by Nova Molecular Technologies Lake Geneva Wi.

The alcohols, marketed under the trade name "Aldol Alcohol" and conform to the following structure;

Nova ALDOL ALCOHOL
$$\underset{R'-CH-CH_2-O-(EO)_x-(PO)_y-(EO)_z-H}{\overset{R''}{|}}$$

R' is $H+CH_2-\underset{R^3}{\overset{|}{CH}}\overset{}{]_n}CH_2(\underset{R^3}{\overset{|}{CH}})-(CH_2)_2-$ R'' is $-O-(CH_2)_4-\underset{R^3}{\overset{|}{CH}}-CH_2-[-\underset{R^3}{\overset{|}{CH}}-CH_2]_m-H$ $R^3$ is hydrogen or lower alkyl;
EO is $-(CH_2CH_2-O)-$
PO is $-(CH_2CH(CH_3)-O)-$
x, y and z are independently integers from 0 to 20;
m is an integer from 0 to 5;
n is an integer from 0 to 5.

| Name | n | m | x | y | z |
|---|---|---|---|---|---|
| ALDOL ALCOHOL 21 | 1 | 1 | 0 | 0 | 0 |
| ALDOL ALCOHOL 27 | 2 | 2 | 0 | 0 | 0 |
| ALDOL ALCOHOL 21-E3 | 1 | 1 | 3 | 0 | 0 |
| ALDOL ALCOHOL 21-E5 | 1 | 1 | 5 | 0 | 0 |
| ALDOL ALCOHOL 21-E15 | 1 | 1 | 15 | 0 | 0 |
| ALDOL ALCOHOL 21-E20 | 1 | 1 | 20 | 0 | 0 |
| ALDOL ALCOHOL 27-P20-E20 | 2 | 2 | 0 | 20 | 20 |
| ALDOL ALCOHOL 27-E10-P10 | 2 | 2 | 10 | 10 | 0 |
| ALDOL ALCOHOL 27-E5-P4 | 2 | 2 | 5 | 4 | 0 |
| ALDOL ALCOHOL 27-E20 | 2 | 2 | 20 | 0 | 0 |

We have learned that esters derived from these alcohols make outstanding viscosity index modifiers. In one embodiment the compounds of the current invention, are monoesters and conform to the following structure;

$$R-C(O)-R$$

wherein $R^1$ is;

$$\underset{R'-CH-CH_2-O-(EO)_x-(PO)_y-(EO)_z-}{\overset{R''}{|}}$$

R' is $H-[-CH_2-\underset{R^3}{\overset{|}{CH}}-]_n-CH_2(\underset{R^3}{\overset{|}{CH}})-(CH_2)_2-$ R'' is R'' is $-O-(CH_2)_4-\underset{R^3}{\overset{|}{CH}}-CH_2-[-\underset{R^3}{\overset{|}{CH}}-CH_2]_m-H$ $R^3$ is hydrogen or lower alkyl;
EO is $-(CH_2CH_2-O)-$
PO is $-(CH_2CH(CH_3)-O)-$
x, y and z are independently integers from 0 to 20;
m is an integer from 0 to 5;
n is an integer from 0 to 5.
R is alkyl having between 6 and 20 carbon atoms.

In another embodiment the compounds of the current invention are diesters of these internal branched ether alcohols and conform to the following structure;

$$R^1-R^2-R^1$$

wherein $R^1$ is;
$R^2$ is selected from;

$$-\overset{O}{\underset{}{\overset{\|}{C}}}-(CH_2)_p-\overset{O}{\underset{}{\overset{\|}{C}}}-$$

or $$-\overset{O}{\underset{}{\overset{\|}{C}}}-(CH_2)_m-CH=CH(CH_2)_o-\overset{O}{\underset{}{\overset{\|}{C}}}-$$

p has a value from 1 to 15;
m and o independently range from 0 to 5;
n is 1 or 3.

In a final embodiment the compounds of the current invention are triesters and conform to the following structure;

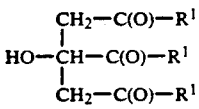

wherein $R^1$ is;

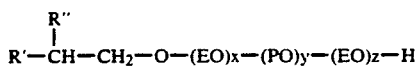

$R'$ is

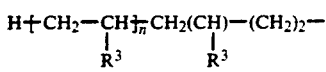

$R''$ is

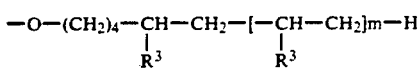

$R^3$ is hydrogen or lower alkyl;
EO is $-(CH_2CH_2-O)-$
PO is $-(CH_2CH(CH_3)-O-$
x, y and z are independently integers from 0 to 20;
m is an integer from 0 to 5;
n is an integer from 0 to 5.

The high molecular weight and the presence an internal branched ether linkage on the alcohol backbone of the compounds of the present invention, make these materials unique in their structure and in their performance properties as viscosity index modifiers.

These alcohols are esterified with fatty acids, citric acid or diacids, using known methods, to give the esters of the present invention.

| | Nova Name |
|---|---|
| Raw Material Alcohols | |
| Example #1 | ALDOL ALCOHOL 21 |
| Example #2 | ALDOL ALCOHOL 27 |
| Example #3 | ALDOL ALCOHOL 21-E3 |
| Example #4 | ALDOL ALCOHOL 21-E5 |
| Example #5 | ALDOL ALCOHOL 21-E15 |
| Example #6 | ALDOL ALCOHOL 21-E20 |
| Example #7 | ALDOL ALCOHOL 27-P20-E20 |
| Example #8 | ALDOL ALCOHOL 27-E10-P10 |
| Example #9 | ALDOL ALCOHOL 27-E5-P4 |
| Example #10 | ALDOL ALCOHOL 27-E20 |
| Suitable Acid Raw Materials | |
| Tallow Acid | Mixture of C18 and C16 |
| Lauric Acid | $C_{12}H_{26}O_2$ |
| Myristic Acid | $C_{14}H_{30}O_2$ |
| Palmitic Acid | $C_{16}H_{34}O_2$ |
| Stearic Acid | $C_{18}H_{38}O_2$ |
| Caprylic Acid | $C_8H_{18}O_2$ |
| Suitable Diacid Raw Materials | |
| Adipic Acid | $HO(O)C(CH_2)_4C(O)OH$ |
| Succinic Acid | $HO(O)C(CH_2)_2C(O)OH$ |
| Dodecanedioic Acid | $HO(O)C(CH_2)_{10}C(O)OH$ |
| Malic Acid | $HO(O)CCH=CHC(O)OH$ |
| Malonic Acid | $HO(O)C(CH_2)_3C(O)OH$ |
| Azelaic Acid | $HO(O)C(CH_2)_5C(O)OH$ |
| Suitable Triacid Raw Materials | |
| Citric Acid | $CH_2-C(O)OH$ |
| | $HO-CH-C(O)OH$ |
| | $CH_2-C(O)OH$ |

EXAMPLES

General Procedure

In a suitable reaction vessel is added the specified Nova ALDOL ALCOHOL (example 1-10). The specified amount of the acid, is then added under good agitation. Next, between 0.1 and 0.5% of an esterification catalyst is added. Begin to heat. The reaction starts as the temperature reaches 140 degrees C. Continue to heat to 200 degrees C. and apply vacuum as the rate of distillation slows. A minimum of 97% of the theoretical water is removed before proceeding. Apply vacuum as the rate of distillation slows. A minimum of 97% of the theoretical water is removed, giving the desired product.

EXAMPLE #11

In a suitable reaction vessel is added 329.0 grams of Nova ALDOL ALCOHOL 21 (example 1), 275.0 grams of tallow fatty acid, under good agitation and nitrogen sparge. Next, add 1.0 gram of stannous oxylate, an esterification catalyst. Begin to heat. The reaction begins as the temperature reaches 140 degrees C. Continue to heat to 200 degrees C. and apply vacuum as the rate of distillation slows. A minimum of 97% of the theoretical water is removed before proceeding. Apply vacuum as the rate of distillation slows. The product is used without additional purification.

EXAMPLES 12-13

Example 11 is repeated, however this time the specified amount of the specified type of acid replaces the tallow acid and the specified amount and type of ALDOL ALCOHOL is used.

| Example Number | ALDOL ALCOHOL Type | Grams | Fatty Acid Type | Grams |
|---|---|---|---|---|
| 12 | Example 1 | 329.0 | Tallow Acid | 286.0 |
| 13 | Example 1 | 329.0 | Lauric Acid | 202.0 |
| 14 | Example 1 | 329.0 | Myristic Acid | 230.0 |
| 15 | Example 1 | 329.0 | Palmitic Acid | 258.0 |
| 16 | Example 1 | 329.0 | Stearic Acid | 286.0 |
| 17 | Example 1 | 329.0 | Caprylic Acid | 146.0 |
| 18 | Example 1 | 329.0 | Adipic Acid | 73.0 |
| 19 | Example 1 | 329.0 | Succinic Acid | 59.0 |
| 20 | Example 1 | 329.0 | Dodecanedioic Acid | 115.0 |
| 21 | Example 1 | 329.0 | Malic Acid | 58.0 |
| 22 | Example 1 | 329.0 | Malonic Acid | 66.0 |
| 23 | Example 1 | 329.0 | Azelaic Acid | 80.0 |
| 24 | Example 1 | 329.0 | Citric Acid | 64.3 |
| 25 | Example 2 | 411.0 | Tallow Acid | 275.0 |
| 26 | Example 2 | 411.0 | Lauric Acid | 202.0 |
| 27 | Example 2 | 411.0 | Myristic Acid | 230.0 |
| 28 | Example 2 | 411.0 | Palmitic Acid | 258.0 |
| 29 | Example 2 | 411.0 | Stearic Acid | 286.0 |
| 30 | Example 2 | 411.0 | Caprylic Acid | 146.0 |
| 31 | Example 2 | 411.0 | Adipic Acid | 73.0 |
| 32 | Example 2 | 411.0 | Succinic Acid | 59.0 |
| 33 | Example 2 | 411.0 | Dodecanedioic Acid | 115.0 |
| 34 | Example 2 | 411.0 | Malic Acid | 58.0 |
| 35 | Example 2 | 411.0 | Citric Acid | 64.3 |

-continued

| Example Number | ALDOL ALCOHOL Type | Grams | Fatty Acid Type | Grams |
|---|---|---|---|---|
| 36 | Example 3 | 461.0 | Tallow Acid | 275.0 |
| 37 | Example 3 | 461.0 | Lauric Acid | 202.0 |
| 38 | Example 3 | 461.0 | Palmitic Acid | 258.0 |
| 39 | Example 3 | 461.0 | Stearic Acid | 286.0 |
| 40 | Example 3 | 461.0 | Succinic Acid | 59.0 |
| 41 | Example 3 | 461.0 | Dodecanedioic Acid | 115.0 |
| 42 | Example 3 | 461.0 | Malonic Acid | 66.0 |
| 43 | Example 3 | 461.0 | Citric Acid | 63.4 |
| 44 | Example 4 | 668.2 | Lauric Acid | 202.0 |
| 45 | Example 4 | 668.2 | Myristic Acid | 230.0 |
| 46 | Example 4 | 668.2 | Palmitic Acid | 258.0 |
| 47 | Example 4 | 668.2 | Stearic Acid | 286.0 |
| 48 | Example 4 | 668.2 | Caprylic Acid | 146.0 |
| 49 | Example 4 | 668.2 | Adipic Acid | 73.0 |
| 50 | Example 4 | 668.2 | Succinic Acid | 59.0 |
| 51 | Example 4 | 668.2 | Dodecanedioic Acid | 115.0 |
| 52 | Example 4 | 668.2 | Malic Acid | 58.0 |
| 53 | Example 4 | 668.2 | Malonic Acid | 66.0 |
| 54 | Example 4 | 668.2 | Azelaic Acid | 80.0 |
| 55 | Example 4 | 668.2 | Citric Acid | 63.4 |
| 56 | Example 5 | 989.1 | Tallow Acid | 275.0 |
| 57 | Example 5 | 989.1 | Lauric Acid | 202.0 |
| 58 | Example 5 | 989.1 | Myristic Acid | 230.0 |
| 59 | Example 5 | 989.1 | Palmitic Acid | 258.0 |
| 60 | Example 5 | 989.1 | Stearic Acid | 286.0 |
| 61 | Example 5 | 989.1 | Caprylic Acid | 146.0 |
| 62 | Example 5 | 989.1 | Adipic Acid | 73.0 |
| 63 | Example 5 | 989.1 | Succinic Acid | 59.0 |
| 64 | Example 5 | 989.1 | Dodecanedioic Acid | 115.0 |
| 65 | Example 5 | 989.1 | Malic Acid | 58.0 |
| 66 | Example 5 | 989.1 | Malonic Acid | 66.0 |
| 67 | Example 5 | 989.1 | Azelaic Acid | 80.0 |
| 68 | Example 5 | 989.1 | Citric Acid | 63.4 |
| 69 | Example 6 | 1209.0 | Tallow Acid | 275.0 |
| 70 | Example 6 | 1209.0 | Lauric Acid | 202.0 |
| 71 | Example 6 | 1209.0 | Myristic Acid | 230.0 |
| 72 | Example 6 | 1209.0 | Palmitic Acid | 258.0 |
| 73 | Example 6 | 1209.0 | Stearic Acid | 286.0 |
| 74 | Example 6 | 1209.0 | Caprylic Acid | 146.0 |
| 75 | Example 6 | 1209.0 | Adipic Acid | 73.0 |
| 76 | Example 6 | 1209.0 | Succinic Acid | 59.0 |
| 77 | Example 6 | 1209.0 | Dodecanedioic Acid | 115.0 |
| 78 | Example 6 | 1209.0 | Malic Acid | 58.0 |
| 79 | Example 6 | 1209.0 | Malonic Acid | 66.0 |
| 80 | Example 6 | 1209.0 | Azelaic Acid | 80.0 |
| 81 | Example 6 | 1209.0 | Citric Acid | 63.4 |
| 82 | Example 7 | 2471.2 | Tallow Acid | 275.0 |
| 83 | Example 7 | 2471.2 | Lauric Acid | 202.0 |
| 84 | Example 7 | 2471.2 | Myristic Acid | 230.0 |
| 85 | Example 7 | 2471.2 | Palmitic Acid | 258.0 |
| 86 | Example 7 | 2471.2 | Stearic Acid | 286.0 |
| 87 | Example 7 | 2471.2 | Caprylic Acid | 146.0 |
| 88 | Example 7 | 2471.2 | Adipic Acid | 73.0 |
| 89 | Example 7 | 2471.2 | Succinic Acid | 59.0 |
| 90 | Example 7 | 2471.2 | Dodecanedioic Acid | 115.0 |
| 91 | Example 7 | 2471.2 | Malic Acid | 58.0 |
| 92 | Example 7 | 2471.2 | Malonic Acid | 66.0 |
| 93 | Example 7 | 2471.2 | Azelaic Acid | 80.0 |
| 94 | Example 7 | 2471.2 | Citric Acid | 63.4 |
| 95 | Example 8 | 1441.0 | Tallow Acid | 275.0 |
| 96 | Example 8 | 1441.0 | Lauric Acid | 202.0 |
| 97 | Example 8 | 1441.0 | Myristic Acid | 230.0 |
| 98 | Example 8 | 1441.0 | Palmitic Acid | 258.0 |
| 99 | Example 8 | 1441.0 | Stearic Acid | 286.0 |
| 100 | Example 8 | 1441.0 | Caprylic Acid | 146.0 |
| 101 | Example 8 | 1441.0 | Adipic Acid | 73.0 |
| 102 | Example 8 | 1441.0 | Succinic Acid | 59.0 |
| 103 | Example 8 | 1441.0 | Dodecanedioic Acid | 115.0 |
| 104 | Example 8 | 1441.0 | Malic Acid | 58.0 |
| 105 | Example 8 | 1441.0 | Malonic Acid | 66.0 |
| 106 | Example 8 | 1441.0 | Azelaic Acid | 80.0 |
| 107 | Example 8 | 1441.0 | Citric Acid | 63.4 |
| 108 | Example 9 | 867.0 | Tallow Acid | 275.0 |
| 109 | Example 9 | 867.0 | Lauric Acid | 202.0 |
| 110 | Example 9 | 867.0 | Myristic Acid | 230.0 |
| 111 | Example 9 | 867.0 | Palmitic Acid | 258.0 |
| 112 | Example 9 | 867.0 | Stearic Acid | 286.0 |
| 113 | Example 9 | 867.0 | Caprylic Acid | 146.0 |
| 114 | Example 9 | 867.0 | Adipic Acid | 73.0 |
| 115 | Example 9 | 867.0 | Succinic Acid | 59.0 |
| 116 | Example 9 | 867.0 | Dodecanedioic Acid | 115.0 |
| 117 | Example 9 | 867.0 | Malic Acid | 58.0 |
| 118 | Example 9 | 867.0 | Malonic Acid | 66.0 |
| 119 | Example 9 | 867.0 | Azelaic Acid | 80.0 |
| 120 | Example 9 | 867.0 | Citric Acid | 63.4 |
| 121 | Example 10 | 1291.0 | Tallow Acid | 275.0 |
| 122 | Example 10 | 1291.0 | Lauric Acid | 202.0 |
| 123 | Example 10 | 1291.0 | Myristic Acid | 230.0 |
| 124 | Example 10 | 1291.0 | Palmitic Acid | 258.0 |
| 125 | Example 10 | 1291.0 | Stearic Acid | 286.0 |
| 126 | Example 10 | 1291.0 | Caprylic Acid | 146.0 |
| 127 | Example 10 | 1291.0 | Adipic Acid | 73.0 |
| 128 | Example 10 | 1291.0 | Succinic Acid | 59.0 |
| 129 | Example 10 | 1291.0 | Dodecanedioic Acid | 115.0 |
| 130 | Example 10 | 1291.0 | Malic Acid | 58.0 |
| 131 | Example 10 | 1291.0 | Malonic Acid | 66.0 |
| 132 | Example 10 | 1291.0 | Azelaic Acid | 80.0 |
| 133 | Example 10 | 1291.0 | Citric Acid | 63.4 |

APPLICATION EXAMPLES

We have evaluated the initial viscosity as well as viscosity variation as a function of temperature of several of the esters of the present invention and several other esters for comparison to the compounds of the present invention.

The following data shows the viscosity effect as a function of temperature. We have chosen products based upon the guerbet alcohol, and the same ester type based upon the branched aldol ether alcohols disclosed. Compounds based upon linear alcohols of compared molecular weight (i.e. stearic) would have been solid. This shows the critical nature of the internal location of the branched ether linkage to liquidity.

This data below shows viscosity of various esters (in centistokes) as a function of temperature (in degrees C.).

| Material | 5 C | 10 C | 20 C | 30 C |
|---|---|---|---|---|
| Triesters | | | | |
| Guerbet (20 Citrate) | 4,392 | 2,600 | 1134 | 673 |
| Tridecyl Citrate | 1,300 | 500 | 350 | 220 |
| Example #24 | 350 | 108 | 74 | 25 |
| Example #35 | 425 | 160 | 91 | 40 |
| Example #43 | 300 | 80 | 60 | 20 |
| Stearyl (4EO) Citrate | Solid | Solid | Solid | Solid |
| Stearyl (4PO) Citrate | Solid | Solid | Solid | Solid |
| Stearyl Citrate | Solid | Solid | Solid | Solid |
| Diesters | | | | |
| Guerbet (20) Dodeacanedioic | 300 | 170 | 70 | |
| Example #20 | 150 | 80 | 30 | |
| Example #33 | 200 | 110 | 50 | |
| Example #41 | 100 | 50 | 26 | |
| Stearyl (4EO) Dodecanedioic | Solid | Solid | Solid | |
| Stearyl (4PO) Dodecanedioic | Solid | Solid | Solid | |
| Stearyl Dodecanedioic | Solid | Solid | Solid | |
| Monoesters | | | | |
| Guerbet (20) Tallowate | 320 | 190 | 57.5 | |
| Example #12 | 150 | 100 | 25.6 | |
| Example #25 | 175 | 125 | 46.0 | |
| Example #36 | 130 | 90 | 20.0 | |
| Stearyl (4EO) Tallowate | Solid | Solid | Solid | |
| Stearyl (4PO) Tallowate | Solid | Solid | Solid | |

| Material | 5 C | 10 C | 20 C | 30 C |
|---|---|---|---|---|
| Stearyl Tallowate | | Solid | Solid | Solid |

The low viscosity over a wide range of temperatures is one of the most important reasons why the compounds of the present invention are outstanding viscosity index modifiers.

What is claimed is:

1. A branched ether ester conforming to the following formula;

$$R-C(O)-R^1$$

wherein $R^1$ is;

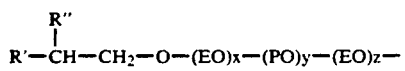

$R'$ is

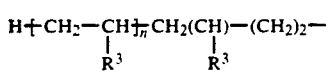

$R''$ is

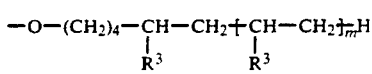

$R^3$ is selected from hydrogen or methyl;
EO is $-(CH_2CH_2-O)-$
PO is $-(CH_2CH(CH_3)-O)-$
x, y and z are independently integers from 0 to 20;
m is an integer from 0 to 5;
n is an integer from 0 to 5;
R is alkyl having between 6 and 20 carbon atoms.

2. A compound of claim 1, wherein R is alkyl having between 12 and 18 carbon atoms.

3. A compound of claim 1, wherein R is alkyl having 18 carbon atoms.

4. A compound of claim 1, wherein x, y and z are all zero.

5. A branched ether ester conforming to the following formula;

$$R^1-R^2-R^1$$

wherein $R^1$ is;

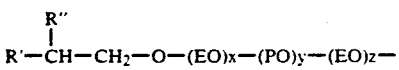

$R'$ is

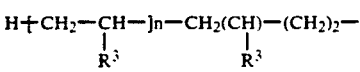

$R''$ is

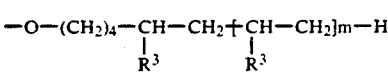

$R^3$ is selected from hydrogen or methyl;
EO is $-(CH_2CH_2-O)-$
PO is $-(CH_2CH(CH_3)-O)-$
x, y, and z, are independently integers from 0 to 20;
$R^2$ is selected from;

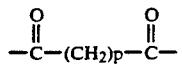

or

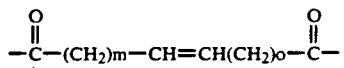

p has a value from 1 to 15;
m and o independently range from 0 to 5;
n is 1 or 3.

6. A compound of claim 5, wherein R is alkyl having between 12 and 18 carbon atoms.

7. A compound of claim 6, wherein R is alkyl having 18 carbon atoms.

8. A compound of claim 6, wherein $R^2$ is;

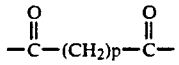

p has a value from 1 to 15.

9. A compound of claim 6, wherein $R^2$ is;

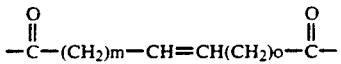

m and o independently range from 0 to 5.

10. An branched ether ester conforming to the following formula;

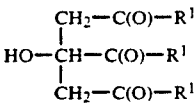

wherein $R^1$ is;

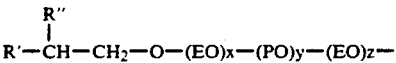

$R'$ is

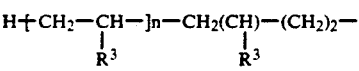

$R''$ is

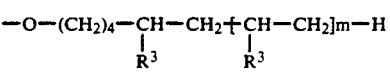

$R^3$ is selected from hydrogen or methyl;
EO is $-(CH_2CH_2-O)-$
PO is $-(CH_2CH(CH_3)-O)-$
x, y and z are independently integers from 0 to 20;

m is an integer from 0 to 5;
n is and integer from 0 to 5.

11. A compound of claim 10 wherein x, y and z are all zero.

12. A compound of claim 10 wherein x, y and z independently range from 1 to 5.

13. A compound of claim 10 wherein m and n are independently integers ranging from 1 to 3.

14. A compound of claim 10 wherein m and n are each 1.

15. A compound of claim 10 wherein m and n are each 0.

* * * * *